(12) United States Patent
Kimura et al.

(10) Patent No.: US 9,314,784 B2
(45) Date of Patent: Apr. 19, 2016

(54) OLEFIN DIMERS AND METHOD FOR PRODUCING AND WASHING OLEFIN DIMERS

(75) Inventors: Nobuhiro Kimura, Tokyo (JP); Tatsuo Hamamatsu, Tokyo (JP)

(73) Assignee: JX NIPPON OIL & ENERGY CORPORATION, Tokyo (JP)

(*) Notice: Subject to any disclaimer, the term of this patent is extended or adjusted under 35 U.S.C. 154(b) by 995 days.

(21) Appl. No.: 13/257,838

(22) PCT Filed: Jan. 21, 2010

(86) PCT No.: PCT/JP2010/050716
§ 371 (c)(1),
(2), (4) Date: Dec. 5, 2011

(87) PCT Pub. No.: WO2010/109935
PCT Pub. Date: Sep. 30, 2010

(65) Prior Publication Data
US 2012/0078022 A1    Mar. 29, 2012

(30) Foreign Application Priority Data

Mar. 26, 2009  (JP) ............... P2009-076861

(51) Int. Cl.
| | | |
|---|---|---|
| C07C 11/12 | (2006.01) |
| C07C 2/02 | (2006.01) |
| B01J 35/02 | (2006.01) |
| B01J 27/182 | (2006.01) |
| B01J 37/02 | (2006.01) |
| C07C 2/18 | (2006.01) |

(52) U.S. Cl.
CPC .............. B01J 35/023 (2013.01); B01J 27/182 (2013.01); B01J 37/0201 (2013.01); C07C 2/18 (2013.01); *C07C 2527/173* (2013.01); *Y02P 20/52* (2015.11)

(58) Field of Classification Search
USPC ......... 585/514, 500, 510, 509, 506, 520, 527, 585/529, 800, 833, 868, 853, 854
See application file for complete search history.

(56) References Cited

U.S. PATENT DOCUMENTS

| | | | | |
|---|---|---|---|---|
| 2,425,340 | A * | 8/1947 | Nixon et al. ............. 585/254 |
| 3,887,634 | A * | 6/1975 | Hughes ............. C07C 2/18 585/527 |
| 5,120,901 | A * | 6/1992 | DiLeo ............. C07C 7/177 585/514 |
| 5,536,689 | A | 7/1996 | Chauvin et al. |
| 6,459,009 | B1 * | 10/2002 | Miller et al. ................. 585/809 |
| 6,770,791 | B2 | 8/2004 | Mathys et al. |
| 2003/0225307 | A1 | 12/2003 | Mathys et al. |
| 2004/0267077 | A1 * | 12/2004 | Ding et al. .................. 585/809 |
| 2008/0027261 | A1 | 1/2008 | Hamamatsu et al. |
| 2009/0099400 | A1 | 4/2009 | Hamamatsu et al. ......... 585/529 |

FOREIGN PATENT DOCUMENTS

| | | | |
|---|---|---|---|
| CN | 1106023 | 8/1995 | |
| CN | 1487909 | 4/2004 | |
| CN | 1997450 | 7/2007 | |
| EP | 1769847 A1 * | 4/2007 | ............... B01J 27/16 |
| EP | 1 894 627 | 3/2008 | |
| JP | 7-59301 B2 | 6/1995 | |
| JP | 8-40946 A | 2/1996 | |
| JP | 8-29251 B2 | 3/1996 | |
| JP | 8-325181 A | 12/1996 | |
| JP | 9-233290 A | 9/1997 | |
| JP | 11-60510 A | 3/1999 | |
| JP | 2001-199907 A | 7/2001 | |
| JP | 2006-51492 A | 2/2006 | |
| JP | 2008-149275 A | 7/2008 | |
| JP | 2009-240969 | 10/2009 | |
| JP | 5190401 | 4/2013 | |
| WO | 2006/126727 | 11/2006 | |

OTHER PUBLICATIONS

Raab, "Caustic scrubbers can be designed for exacting needs", Oil and Gas Journal (1976), 74(41), 120-125—month unknown.*
Office Action for counterpart JP Patent Application No. 2009-076861, mailed on May 7, 2013.
Office Action issued with respect to Chinese Patent Application No. 201080013548.X, dated Jun. 27, 2013.
Fabrizio Cavani et al., "Effect of water in the performance of the "solid phosphoric acid" catalyst for alkylation of benzene to cumene and for oligomerization of propene", Applied Catalysis A: General, vol. 97, (1993). Elsevier Science Publishers B.V., Amsterdam, 1993, pp. 177-196.
Search report from International Patent Application No. PCT/JP2010/050716, mail date is Feb. 23, 2010.
International Preliminary Report on Patentability for International Patent Application No. PCT/JP2010/050716, mail date is Oct. 27, 2011.
Notice of Allowance in counterpart JP Patent Application No. P2009-076861, mailed on Jul. 23, 2013.
Office Action for GC Application No. GC 2010-15396, which was dispatched on Apr. 15, 2014.

* cited by examiner

*Primary Examiner* — In Suk Bullock
*Assistant Examiner* — Ali Z Fadhel
(74) *Attorney, Agent, or Firm* — Greenblum & Bernstein, P.L.C.

(57) ABSTRACT

The process for producing an olefin dimer of the present invention includes a first step of carrying out a dimerization reaction of an olefin in the presence of a solid phosphoric acid catalyst in which phosphoric acid is supported on inorganic support particles at a reaction temperature of 55 to 300° C. by introducing into a reactor an olefin-containing raw material containing water in an amount of 10 ppm by mass or more and less than the saturated water content at the reaction temperature, thereby preparing a reaction product containing an olefin dimer, a second step of washing the reaction product prepared in the first step at a temperature of 50° C. or higher using an alkaline substance-containing water adjusted to pH 8 to 13 and a third step of washing the reaction product after the alkaline washing in the second step with water at a temperature of 0 to 110° C., thereby preparing an olefin dimer.

7 Claims, No Drawings

OLEFIN DIMERS AND METHOD FOR PRODUCING AND WASHING OLEFIN DIMERS

TECHNICAL FIELD

The present invention relates to a process for producing an olefin dimer using a solid phosphoric acid catalyst and an olefin dimer produced by the process.

BACKGROUND ART

Solid phosphoric acid catalysts in which phosphoric acid is supported on an inorganic support are widely used in the hydration reaction or oligomerization reaction of olefins.

On the other hand, oligomers of olefins are used in various applications and dimers of light olefins (for example, propylene, n-butene, isobutane and pentene) are particularly important as high octane number base materials for gasoline or chemical intermediate raw materials. Oligomerization reactions including dimerization of olefins are carried out using an acid catalyst and many studies have been done on them. Typical examples of acid catalysts include liquid or gas catalysts such as sulfuric acid, hydrofluoric acid, phosphoric acid, aluminum chloride and boron fluoride and solid catalysts such as amorphous or crystalline aluminosilicate, clay, ion exchange resin, composite oxide and acid supported on a support. The above-described solid phosphoric acid catalysts which can be produced by an inexpensive and easy process have also been extensively studied.

Examples of oligomerization reactions of olefin by a solid phosphoric acid catalyst proposed include a process for oligomerizing propylene using a solid phosphoric acid catalyst prepared under a calcination condition of higher than 100° C. (see, for example, patent document 1) and a process for oligomerizing propylene using a catalyst (composed of silicon orthophosphate and silicon pyrophosphate) prepared by crystallizing an amorphous mixture of phosphoric acid and a siliceous raw material at 250 to 450° C. in an atmosphere of an air-water vapor mixed gas at a water vapor concentration of 3 to 50% by mole (see, for example, patent document 2). Also, the influence of the condensation degree of phosphoric acid in a solid phosphoric acid catalyst on the activity of oligomerization reaction of olefin has been known. For example, patent document 3 and non-patent document 1 disclose a process for oligomerizing C3 or C4 olefin using a catalyst in which the weight ratio of free phosphoric acid components (non- or low-condensed phosphoric acid such as orthophosphoric acid and pyrophosphoric acid) eluted when immersing a solid phosphoric acid catalyst in water to the catalyst is small (the ratio of orthophosphoric acid to phosphoric acid supported being about 46% by mole at most in terms of phosphorus atoms).

However, none of the above conventional oligomerization reactions of olefin using a solid phosphoric acid catalyst is primarily directed to dimerization of olefin, and by-production of a highly polymerized product of olefin was inevitable when using a conventional solid phosphoric acid catalyst, making selective production of olefin dimer difficult.

There are studies on improvement of the selectivity of dimerization of olefin; for example, patent document 4 proposes a process for dimerizing olefin using a solid phosphoric acid catalyst in which the ratio of orthophosphoric acid to phosphoric acid supported on a support is 60% by mole or more in terms of phosphorus atoms.

On the other hand, it is unknown that in oligomerization reaction of olefin using a solid phosphoric acid catalyst, a reaction solution obtained at the outlet of a reactor contains phosphoric acid eluted from the catalyst and the amount of elution varies depending on the temperature of the oligomerization reaction. And there is no finding on controlling the amount of elution by selecting the temperature of the oligomerization reaction.

Moreover, phosphoric acid eluted into the reaction solution is concentrated when separating LPG fraction and oligomer or oligomer and heavy substances in a distillation column or the like in the downstream stage of an oligomerization reaction process, possibly causing corrosion of the apparatus. For that reason, effective removal of phosphoric acid in the reaction solution is desired.

CITATION LIST

Patent Literature

[Patent document 1] Japanese Examined Patent Publication No. 8-29251
[Patent document 2] Japanese Examined Patent Publication No. 7-59301
[Patent document 3] Japanese Patent Laid-Open No. 2001-199907
[Patent document 4] Japanese Patent Laid-Open No. 2006-51492
[Patent document 5] Japanese Patent Laid-Open No. 9-233290

Non-Patent Literature

[Non-patent document 1] "Applied Catalysis A: General", 1993, 97, p. 177-496

DISCLOSURE OF THE INVENTION

Problems to be Solved by the Invention

The present inventors have found that, when dimerizing an olefin, using a solid phosphoric acid catalyst, a small amount of phosphoric acid (including those which changes to phosphoric acid by hydrolysis) is eluted into the reaction solution from the catalyst. Since the small amount of phosphoric acid causes corrosion of devices, the important problem is to remove the phosphoric acid in the reaction solution. For efficient production of olefin dimer, it is desirable to not only improve the catalytic activity of a solid phosphoric acid catalyst and the selectivity of dimerization of olefin but also be able to easily remove phosphoric acid eluted. However, Japanese Patent Laid-Open No. 2006-51492 does not disclose the elution of phosphoric acid into a reaction solution nor does it disclose the removal of phosphoric acid eluted, although it describes the relationship between the composition of phosphoric acid of a solid phosphoric acid catalyst and the selectivity of dimerization.

Also, adding a substantial amount of water to raw materials is an effective way to prevent the reduction of catalytic activity when dimerizing an olefin using a solid phosphoric acid catalyst. Since some of the water reacts with olefin in the raw materials to produce an oxygen-containing compound such as alcohol or ketone as a by-product, another important problem is to remove such an oxygen-containing compound especially when producing an olefin dimer as a chemical intermediate raw material. For efficient production of olefin dimer, it is desirable to not only maintain the catalytic activity of a solid phosphoric acid catalyst but also be able to easily remove by-product oxygen-containing compounds. However, Japanese Patent Laid-Open No. 2006-51492 does not disclose the removal of by-product oxygen-containing compounds although it describes the relationship between the composition of phosphoric acid of a solid phosphoric acid catalyst and the selectivity of dimerization.

Under such circumstances, an object of the present invention is to provide a process for producing an olefin dimer at a high selectivity using a solid phosphoric acid catalyst, a process for efficiently producing an olefin dimer by controlling the amount of elution of phosphoric acid into a reaction product in a dimerization reaction of an olefin using a solid phosphoric acid catalyst and easily removing the phosphoric acid catalyst eluted or an oxygen-containing compound produced as a by-product and mixed in the reaction product in the dimerization reaction, and an olefin dimer produced by the process.

Means for Solving the Problems

The present inventors have conducted intensive studies to solve the above-described problems and as a result have found that, in a dimerization reaction of an olefin using a solid phosphoric acid catalyst supported on inorganic support particles, the elution of phosphoric acid into a reaction product can be controlled by allowing to react under a specific temperature condition, and phosphoric acid eluted and a by-product oxygen-containing compound can be efficiently removed by washing the reaction product under a specific condition. More specifically, the present inventors have found that the amount of phosphoric acid eluted into the reaction solution is kept low by setting temperatures of the dimerization reaction of an olefin to 55° C. or higher and the phosphoric acid eluted and a by-product oxygen-containing compound can be efficiently removed by washing the phosphoric acid eluted into the reaction solution with alkali in a specific pH and temperature range and then by washing with water in a specific temperature range, and have completed the present invention.

Accordingly, the present invention provides processes of producing an olefin dimer described in the following (1) to (9) and an olefin dimer described in the following (10).

(1) A process for producing an olefin dimer comprising a first step of carrying out a dimerization reaction of an olefin in the presence of a solid phosphoric acid catalyst in which phosphoric acid is supported on inorganic support particles at a reaction temperature of 55 to 300° C. by introducing into a reactor an olefin-containing raw material containing water in an amount of 10 ppm by mass or more and less than the saturated water content at the reaction temperature, thereby preparing a reaction product containing an olefin dimer, a second step of washing the reaction product prepared in the first step at a temperature of 50° C. or higher using an alkaline substance-containing water adjusted to pH 8 to 13 and a third step of washing the reaction product after the alkaline washing in the second step with water at a temperature of 0 to 110° C., thereby preparing an olefin dimer.

(2) The process according to (1), wherein, regarding the solid phosphoric acid catalyst, a ratio of orthophosphoric acid to the phosphoric acid is 60% by mole or more in terms of phosphorus atoms.

(3) The process according to (1) or (2), wherein the inorganic support particles have an average particle size of 3.0 mm or less.

(4) The process according to any one of (1) to (3), wherein the olefin-containing raw material used in the first step has a water content of 100 ppm by mass or more and less than the saturated water content at a reaction temperature.

(5) The process according to any one of (1) to (4), wherein in the second step the reaction product is washed at a temperature of 80° C. or higher.

(6) The process according to any one of (1) to (5), wherein in the first step the dimerization reaction is carried out in liquid phase.

(7) The process according to any one of (1) to (6), wherein in the third step the reaction product after alkaline washing is washed with water so as to remove an oxygen-containing compound selected from alcohol, ketone, ether and ester having 3 to 7 carbon atoms.

(8) The process according to any one of (1) to (7), wherein in the third step the reaction product is washed with water at a temperature of 0 to 50° C.

(9) The process according to any one of (1) to (8), wherein the olefin is a monoolefin having 3 to 7 carbon atoms.

(10) An olefin dimer produced by the process according to any one of (1) to (9).

Effect of the Invention

The present invention makes it possible to provide a process for a dimerization reaction of an olefin using a solid phosphoric acid catalyst supported on inorganic support particles, in which the dimerization reaction of an olefin is efficiently performed in simple equipment and phosphoric acid eluted and a polar substance such as a by-product oxygen-containing compound can be efficiently removed.

BEST MODES FOR CARRYING OUT THE INVENTION

In the following, preferred embodiments of the present invention will be described in more detail.

The process for producing an olefin dimer according to this embodiment includes the steps shown in the following (I) to (III).

(I) A dimerization reaction step of carrying out a dimerization reaction of an olefin in the presence of a solid phosphoric acid catalyst in which phosphoric acid is supported on inorganic support particles at a reaction temperature of 55 to 300° C. by introducing into a reactor an olefin-containing raw material containing water in an amount of 10 ppm by mass or more and less than the saturated water content at the reaction temperature, thereby preparing a reaction product containing an olefin dimer.

(II) An alkaline washing step of washing the reaction product prepared in the step (I) at a temperature of 50° C. or higher using an alkaline substance-containing water adjusted to pH 8 to 13.

(III) A water washing step of washing the reaction product after alkaline washing in the step (II) with water at a temperature of 0 to 110° C., thereby preparing an olefin dimer.

In the following, the steps (I) to (III) will be described in detail.

<(I) Dimerization Reaction Step>

The catalyst used in this step is a solid phosphoric acid catalyst in which phosphoric acid is supported on inorganic support particles. Inorganic support particles used for the solid phosphoric acid catalyst are not particularly limited as long as they are capable of supporting phosphoric acid. Preferred examples thereof include molded particles of siliceous supports such as diatomaceous earth, infusorial earth, ciliate earth, kieselguhr, kaolin, fuller's earth and artificial porous silica and a mixture thereof. When molding the support, calcination can be performed in any temperature condition so as to achieve a sufficient strength, pore capacity and specific surface area. Methods of molding and shapes of molded articles are not particularly limited. For example, molded particles of a granular shape, a sheet shape or a pellet shape may be prepared by means of tabletting, extrusion molding, spray drying, rolling granulation or granulation in oil.

The aforementioned inorganic support particles have an average particle size of preferably 3.0 mm or less, more preferably 0.5 to 3.0 mm. Inorganic support particles having an average particle size of less than 0.5 mm are not preferred because they cause an increase of the pressure loss in the reactor. On the other hand, inorganic support particles having an average particle size of more than 3.0 mm tend to make it difficult for a reaction fluid to be uniformly dispersed on the surface of the catalyst, causing more fluid to flow on the tube wall of the reactor. As a result, the rate of effective utilization of the catalyst may be decreased and the activity of the dimerization reaction may be decreased. Moreover, because it takes longer time for a substance present at the center of catalyst particles to be diffused away from the catalyst particles, olefin dimers produced by the catalytic action of phosphoric acid at the center of catalyst particles stay longer time in the catalyst particles, making it more likely for the olefin dimers to become a heavy substance of a trimer or higher oligomer by the catalytic action of phosphoric acid. This may cause a decrease of the selectivity in dimerization. The average particle size of 0.5 mm or more and 3.0 mm or less, however, means a range preferred in the present invention. Depending on the level of requirement relating to the above-described disadvantages, a support having a particle size beyond the range may also be used.

The average particle size of inorganic support particles in the present invention means an arithmetic mean of the diameters of 25 randomly selected inorganic support particles measured one by one.

Phosphoric acid constituting the solid phosphoric acid catalyst used in this embodiment is preferably one in which the ratio of orthophosphoric acid is 60% by mole or more in terms of phosphorus atoms. In other words, those in which the ratio of phosphorus atoms in orthophosphoric acid to the number of moles of phosphorus atoms in the whole phosphoric acid supported is 60% by mole or more are preferred. Excellent activity and selectivity are likely to be achieved in the dimerization reaction of olefin with such catalysts. The ratio is more preferably 70% by mole or more, further preferably 80% by mole or more. To maintain a high dimerization reaction activity and high dimer selectivity for long time in a dimerization reaction of olefin, the key is the ratio between orthophosphoric acid and other condensed polyphosphoric acids in phosphoric acid. A preferred method is to make olefin contact with a catalyst with the ratio of orthophosphoric acid to phosphoric acid in the catalyst being 60% by mole or more.

Examples of phosphoric acid used for preparing a solid phosphoric acid catalyst in this embodiment include orthophosphoric acid and condensates thereof, i.e., pyrophosphoric acid and polyphosphoric acid. Those which are formed into phosphoric acid by hydrolysis (phosphoric acid precursors), for example, phosphoric acid esters of alcohol having 1 to 8 carbon atoms may also be used. A mixture thereof may also be used.

For the method of allowing phosphoric acid to be supported on inorganic support particles, a method in which inorganic support particles are immersed in an aqueous phosphoric acid solution and the resultant is dried or a method in which a paste prepared by mixing an inorganic support and an aqueous phosphoric acid solution is molded and dried is generally used. The former method is particularly preferred because phosphoric acid can be appropriately supplied by immersing the catalyst again when the amount of phosphoric acid supported is decreased by the elution of phosphoric acid in the catalyst into the reaction solution during a dimerization reaction. The latter method may be performed simultaneously with molding of inorganic support particles depending on the method of molding and the shape of molded articles.

The content of phosphoric acid in the solid phosphoric acid catalyst is not particularly limited, and the ratio of the mass of phosphoric acid in terms of orthophosphoric acid to the mass of inorganic support particles is preferably 40 to 200% by mass. When the ratio is less than 40% by mass, the activity is decreased or the amount of catalyst required is increased, causing the problem of large equipment cost. When the ratio is more than 200% by mass, it becomes difficult to bring the ratio of orthophosphoric acid to the whole phosphoric acid supported on inorganic support particles to 60% by mole or more.

As a specific embodiment of preparing a catalyst, a method of allowing phosphoric acid to be supported on inorganic support particles by immersing the inorganic support particles in an aqueous phosphoric acid solution and drying will be described. Devices used for preparing the catalyst are not particularly limited and a general batch tank may be used. A method using a reactor for dimerization reaction of olefin is preferred because it is possible to load the reactor with the catalyst while simultaneously preparing the catalyst in the reactor. The aqueous phosphoric acid solution used for the immersion has a concentration of generally about 10 to 85% by mass. The concentration is preferably changed depending on the desired amount of phosphoric acid supported. The time of immersion is generally not particularly limited as long as it is about 1 hour or more. The temperature of immersion is 100° C. or lower, preferably 50° C. or lower. Temperature conditions of higher than 100° C. are not preferred because the ratio of orthophosphoric acid to phosphoric acid may be decreased. Also, since immersion becomes impossible because of coagulation when the temperature is too low, the temperature is preferably 0° C. or higher, more preferably 15° C. or higher.

After immersion, the excess aqueous phosphoric acid solution which has not been supported is removed by a general method such as filtering, and then the resultant is dried by removing the remaining excess water. For drying, gas flow or liquid flow may be used. While fluids used for drying are not particularly limited, air, nitrogen gas, hydrogen gas, saturated hydrocarbon gas having 1 to 5 carbon atoms and saturated hydrocarbon liquid having 2 to 20 carbon atoms are preferred. Also, those fluids may contain water of the saturation amount or less. For example, the resultant may be dried using liquid butane containing 100 ppm by mass or less of water at room temperature. The temperature of drying is 100° C. or lower, more preferably 50° C. or lower. A temperature of higher than 100° C. is not preferred because rapid condensation of phosphoric acid occurs, resulting in a decrease in the ratio of orthophosphoric acid to phosphoric acid. Also, since drying efficiency is decreased when the temperature is too low, the temperature is preferably 0° C. or higher, more preferably 5° C. or higher. The time of drying and the amount of fluid used are appropriately adjusted with observing the progress of condensation of phosphoric acid by drying so that the ratio of orthophosphoric acid to phosphoric acid does not become less than 60% by mole in terms of phosphorus atoms. A highly condensed phosphoric acid catalyst in which condensation of phosphoric acid has progressed may be brought back to a low condensation state (having a ratio of orthophosphoric acid of 60% by mole or more) by immersing again.

In the dimerization reaction of olefin, the solid phosphoric acid catalyst has a water content of preferably 5% by mass or more based on the mass of the solid phosphoric acid catalyst.

When feeding an olefin-containing raw material to the dimerization reaction step, the water content in the olefin-containing raw material is adjusted to 10 ppm by mass or more based on the total amount of the raw material and less than the saturated water content of the raw material at the reaction temperature. This prevents the condensation of phosphoric acid in the catalyst which gradually progresses with the progress of the reaction, making it possible to sufficiently increase the yield of olefin dimers. The water content in the raw material can be adjusted by allowing water to coexist in the reaction system. Methods of supplying water are not particularly limited and examples thereof include a method in which a predetermined amount of water is dissolved in an olefin-containing raw material by a mixing device and the resultant is supplied to the reactor. The water content in the olefin-containing raw material needs to be less than the saturated water content of the olefin-containing raw material at the reaction temperature. Moreover, it is necessary to select the most suitable amount of addition depending on the olefin concentration in the raw material and reaction conditions such as reaction temperatures. When the amount of water added is not less than the saturated water content, the amount is not preferred because condensed water makes phosphoric acid on the catalyst flow out. Also, to ensure the prevention of condensation of phosphoric acid, it is desired that the water content in the olefin-containing raw material is 100 ppm by mass or more and less than the saturated water content of the raw material at the reaction temperature based on the mass of the raw material.

Reactors and types of reaction used in this step are not particularly limited. A batch system, a semi-batch system using vessel type reactor, or a continuous flow type reaction system using a continuous flow reactor such as a fixed bed reactor, a fluidized bed reactor or a moving bed reactor may be employed. The reaction temperature is 55 to 300° C., preferably 55 to 200° C. A temperature of lower than 55° C. is not preferred because elution of phosphoric acid is significantly increased. A temperature of higher than 300° C. is not preferred because more side reactions such as a decomposition reaction of products are caused. The reaction pressure is preferably atmospheric pressure to 20 MPa. When the pressure is lower than atmospheric pressure, the reaction system may not be kept in liquid phase. When the pressure is higher than 20 MPa, it results in an undesirable increase in equipment cost. The reaction time in a continuous flow reaction system is 0.1 to 100 $hr^{-1}$, preferably 0.3 to 30 $hr^{-1}$ in terms of LHSV. An LHSV of lower than 0.1 $hr^{-1}$ is not preferred because production efficiency is decreased or the equipment becomes large, and an LHSV of higher than 100 $hr^{-1}$ is not preferred because the reaction becomes difficult to progress. The reaction time in a batch reaction system, on the other hand, is preferably 0.01 to 10 hours depending on the olefin concentration in the raw material or the raw material/catalyst ratio.

Olefin in the raw material used for the dimerization reaction in this step is preferably a linear, branched or cyclic mono-olefin having 3 to 5 carbon atoms. The olefin may be a single olefin or a mixture of two or more olefins depending on the intended product. Specific examples of olefins include propylene, 1-butene, cis-2-butene, trans-2-butene, isobutylene, n-pentene, isopentene, cyclopentene and any combination of two or more of them. The dimerization reaction of olefin refers to generation of 1 mole of olefin by the reaction of 2 moles of raw material olefin (including the reaction between different olefins when using a raw material of mixed olefins).

To remove the heat of reaction, an olefin-containing raw material containing a solvent may be used. Such solvents are not particularly limited as long as they are in the form of liquid under the dimerization reaction conditions and substantially inert to the solid phosphoric acid catalyst. For example, hydrocarbons such as n-paraffin, isoparaffin, naphthenes and aromatics may be preferably used. Also, a paraffin fraction, which is collected as an unreacted product after the dimerization reaction step and contains olefin at a lower concentration than that of the raw material, or a saturated hydrocarbons such as butane in C4 fraction, may be used as a solvent. For the ratio between olefin and solvent, the ratio of olefin in the total mass of the olefin-containing raw material containing olefin and solvent is 1 to 60% by mass, preferably 10 to 50% by mass and more preferably 15 to 45% by mass. When the ratio of olefin is lower than the lower limit, production efficiency is decreased, and when the ratio of olefin is higher than the upper limit, the calorific value of the dimerization reaction becomes higher, making it difficult to control the reaction temperature.

In this step, preferably a solid phosphoric acid catalyst is brought into contact with an olefin-containing raw material in liquid phase. Contact in gas phase is not preferred because it may cause coking, resulting in a decrease in the activity and selectivity of the dimerization reaction of olefin and a shortening of the life of the catalyst.

<(II) Alkaline Washing Step>

This step is for removing phosphoric acid (including those which changes to phosphoric acid by hydrolysis) eluted into the dimerization reaction product from the solid phosphoric acid catalyst in the dimerization reaction step by washing with an alkaline aqueous solution prepared by adding an alkaline substance to water. In this step, by washing a hydrocarbon liquid obtained in the dimerization reaction step with an alkaline aqueous solution, phosphoric acid in the hydrocarbon liquid derived from the solid phosphoric acid catalyst is extracted with the alkaline aqueous phase, preventing phosphoric acid from being incorporated into the downstream equipment such as a distillation column. Since phosphoric acid is highly corrosive, inexpensive steel products such as carbon steel are easily corroded under conditions of higher than 100° C. Although such corrosion can be prevented by lining devices with a corrosion resistant material such as Hastelloy or tantalum, these corrosion resistant materials are very expensive. The previous removal of eluted phosphoric acid eliminates the need to use such expensive materials, providing a substantial economic benefit. The method of washing and removing phosphoric acid with an alkaline aqueous solution in this embodiment includes a very simple procedure of oil-water separation, contributing to the improvement of economical efficiency.

The desired concentration of phosphoric acid in the dimerization reaction product after water washing resulting from the subsequent water washing step (step (III)) is less than 0.1 ppm by mass. To achieve this, it is desired that the concentration of phosphoric acid after washing and removing with an alkaline aqueous solution in this step is 0.2 ppm by mass or less. When the phosphoric acid concentration at the outlet of this step is more than 0.2 ppm, it becomes difficult to adjust the phosphoric acid concentration in the dimerization reaction product after the subsequent third step of water washing to less than 0.1 ppm by mass. When the phosphoric acid concentration after the third step is 0.1 ppm by mass or more, the phosphoric acid concentration is increased by the subsequent concentration procedure such as distillation, possibly causing corrosion of apparatus.

Examples of alkaline substances described above include hydroxides of alkali metal such as sodium hydroxide, potassium hydroxide and calcium hydroxide.

The alkaline aqueous solution in this step has a pH of 8 to 13, preferably 9 to 13, and more preferably 9 to 12. When the alkaline aqueous solution has a pH of lower than 8, efficient removal of phosphoric acid may be difficult. When the alkaline aqueous solution has a pH of higher than 13, alkaline components are dissolved into the dimerization reaction product after alkaline washing, causing more alkaline components to be incorporated into the subsequent water washing step. The alkaline components incorporated into the water washing step may cause undesirable corrosion of devices. The ratio of the amount of water to that of alkaline substances is not particularly limited as long as the above-described pH can be achieved.

The temperature in this step is 50° C. or higher, preferably 80 to 120° C. When the temperature is lower than 50° C., sufficient removing effect can not be achieved. When the temperature is higher than 120° C., more heat sources such as steam are required although there is no difference in the removing effect. The pressure in the washing step is preferably atmospheric pressure to 20 MPa. When the pressure is higher than 20 MPa, it results in an undesirable increase in equipment cost. When washing using a continuous flow system, LHSV is preferably 0.1 to 100 hr$^{-1}$, more preferably 0.3 to 30 hr$^{-1}$. An LHSV of lower than 0.1 hr$^{-1}$ is not preferred because production efficiency is decreased or the equipment becomes large, and an LHSV of higher than 100 hr$^{-1}$ is not preferred because it becomes difficult to achieve a sufficient removing effect. A preferred washing time when using a batch reactor such as a tank reactor equipped with stirrer is 0.01 to 1 hour.

Methods of washing in this step are not particularly limited, and a method of washing by stirring in a drum equipped with a stirrer or a method in which liquid-liquid contact is efficiently carried out by a mixer in a line based on a continuous flow system may be selected.

<(III) Water Washing Step>

This step is a water washing step of washing the dimerization reaction product after alkaline washing prepared in the aforementioned alkaline washing step (2) with water, thereby removing a polar substance in the dimerization reaction product after alkaline washing and an alkaline substance dissolved into the dimerization reaction product after alkaline washing in the aforementioned alkaline washing step (2). The polar substance to be removed in this water washing step means a substance which has been mixed into the dimerization reaction product in the aforementioned dimerization reaction step (1) and has not been removed and has remained in the aforementioned alkaline washing step (2).

In this step, by washing a hydrocarbon liquid obtained in the alkaline washing step (2) with water, an alkaline substance and a polar substance such as an oxygen-containing compound in the dimerization reaction product are extracted to the water phase. As a result, not only corrosion of the downstream distillation column by the alkaline substance can be prevented but also the amount of the oxygen-containing compound mixed into the final product can be reduced.

The temperature in this step is 0 to 110° C., preferably 0 to 80° C. The temperature is more preferably 0 to 50° C. A temperature of higher than 110° C. is not preferred because a sufficient effect of removing a polar substance cannot be achieved. A temperature of 0° C. or lower is not preferred because water used for washing freezes. The pressure in the water washing step is preferably atmospheric pressure to 20 MPa. When the pressure is higher than 20 MPa, it results in an undesirable increase in equipment cost. When washing with water using a continuous flow system, LHSV is preferably 0.1 to 100 hr$^{-1}$, more preferably 0.3 to 30 hr$^{-1}$. An LHSV of lower than 0.1 hr$^{-1}$ is not preferred because production efficiency is decreased or the equipment becomes large, and an LHSV of higher than 100 hr$^{-1}$ is not preferred because it becomes difficult to achieve a sufficient removing effect. A preferred contact time when using a batch reactor such as a tank reactor equipped with stirrer is 0.01 to 1 hour.

Examples of oxygen-containing compounds in the dimerization reaction product after washing in the alkaline washing step (2), which are to be washed in this step include alcohols such as 1-propanol, 2-propanol, 1-butanol, 2-butanol, isobutanol, tert-butanol, 1-pentanol, 2-pentanol, 3-pentanol, tert-amyl alcohol, 2-methyl-1-butanol, 3-methyl-1-butanol and 3-methyl-2-butanol, ketones such as acetone, methyl ethyl ketone, methyl isobutyl ketone and methyl tert-butyl ketone, ethers such as dimethyl ether, methyl ethyl ether and diethyl ether, and esters such as propyl phosphate, sec-butyl phosphate and tert-butyl phosphate. While one of the compounds may be present alone or two or more of them may coexist, they are both to be washed and removed in this washing step.

Methods of washing in this step are not particularly limited, and a method of washing by stirring in a drum or a method in which liquid-liquid contact is efficiently carried out by a mixer in a line may be selected.

The olefin dimer prepared by the process according to this embodiment contains a reduced amount of polar substances such as an oxygen-containing compound which is a by-product. Since the amount of an oxygen-containing compound in the olefin dimer according to this embodiment has been significantly reduced, the olefin dimer can be suitably used as a chemical intermediate raw material. Also, since phosphoric acid eluted and mixed from the solid phosphoric acid catalyst has been removed from the dimerization reaction product prepared through the above-described three steps, there is no possibility of the corrosion of the subsequent apparatus such as a distillation column, and therefore stable and economically efficient production of olefin dimer becomes possible.

In the following, the present invention will be described in more detail by means of Examples and Comparative Examples, but the present invention is not limited to the following Examples.

EXAMPLES

<Preparation of Catalyst>
(Solid Phosphoric Acid Catalyst A)

40 ml of inorganic support particles, i.e., substantially spherical synthetic silica granules having an average particle size of 2.3 mm, was immersed in 100 ml of a 40% by mass phosphoric acid aqueous solution in a beaker with a capacity of 200 ml. After immersing for 1 hour, the aqueous solution was removed with a mesh filter to prepare a solid phosphoric acid catalyst A. The above procedures were all performed at room temperature.

As a result of analysis of phosphorus ($^{31}$P) in the catalyst A by solid nuclear magnetic resonance spectroscopy, the phosphoric acid supported had a composition (mole % in terms of phosphorus atoms, hereinafter the same as above) of 85% of orthophosphoric acid, 15% of pyrophosphoric acid and no polyphosphoric acid. Also, as a result of neutralization titration, the catalyst A contained 34.4% by mass of phosphoric acid in terms of orthophosphoric acid. After removing phosphoric acid by washing the catalyst A with water and drying, the ratio of the mass of the support to the total mass of the catalyst A was 66.2% by mass.

The average particle size of synthetic silica particles, the support, was determined by the following method. Specifically, particle diameters of 25 support particles were measured and the average was calculated (hereinafter the same as above).

Table 1 shows the average particle size (mm) of the inorganic support particles and the composition of phosphoric acid.

(Solid Phosphoric Acid Catalyst B)

Solid phosphoric acid catalyst B was prepared in the same manner as in preparing the solid phosphoric acid catalyst A except for using substantially spherical synthetic silica granules having an average particle size of 3.5 mm as inorganic support particles. The phosphoric acid supported had a composition of 85% of orthophosphoric acid, 15% of pyrophosphoric acid and no polyphosphoric acid. The catalyst B contained 34.4% by mass of phosphoric acid in terms of orthophosphoric acid and had a ratio of the support of 66.2% by mass.

Table 1 shows the average particle size (mm) of the inorganic support particles and the composition of phosphoric acid.

(Solid Phosphoric Acid Catalyst C)

40 ml of inorganic support particles, i.e., substantially spherical synthetic silica granules having an average particle size of 2.3 mm, was immersed in 100 ml of a 40% by mass phosphoric acid aqueous solution in a beaker with a capacity of 200 ml. After immersing for 1 hour, the aqueous solution was removed with a mesh filter and dried in a drying oven at 110° C. to prepare a solid phosphoric acid catalyst C. The phosphoric acid supported had a composition of 57% of orthophosphoric acid, 38% pyrophosphoric acid and 5% of polyphosphoric acid. The catalyst C contained 34.7% by mass of phosphoric acid in terms of orthophosphoric acid and had a ratio of the support of 66.7% by mass.

Table 1 shows the average particle size (mm) of the inorganic support particles and the composition of phosphoric acid.

TABLE 1

| catalyst | | A | B | C |
|---|---|---|---|---|
| average particle size of inorganic support cuticles (mm) | | 2.3 | 3.5 | 2.3 |
| composition of phosphoric acid | ratio of orthophosphoric acid (mole %) | 85 | 85 | 57 |
| | ratio of pyrophosphoric acid (mole %) | 15 | 15 | 38 |
| | ratio of polyphosphoric acid (mole %) | 0 | 0 | 5 |

Example 1

A stainless steel tubular reactor (inner diameter: 12 mm) was charged with 20 ml of the solid phosphoric acid catalyst A. Dimerization reaction was performed with supplying a butene mixed raw material (35% by mass of isobutylene, 2% by mass of n-butene, 1% by mass of propylene and 62% by mass of butane) to which 300 ppm by mass of water was added based on the mass of the mixed raw material from the top of the reactor at an LHSV of 7 h$^{-1}$ and discharging the products from the bottom. The system maintained its liquid state at a pressure of 5.0 MPa and a temperature at the inlet of the catalyst bed of 90° C. (step 1). Table 2 shows the results of the reaction 24 hours after the start of supplying the butene mixed raw material. The above-described water content is less than the saturated water content at 90° C. of about 2200 ppm by mass.

In Table 2, "total butene conversion (%)", "selectivity of butene dimer (%)" and "yield of butene dimer (%)" are calculated by the following formulas.

Total butene conversion (%)=[1−(total mass concentration of butene in product/total mass concentration of butene in raw material)]×100

Selectivity (%) of butene dimer=(mass concentration of butene dimer in product/(total mass concentration of butene in raw material−total mass concentration of butene in product)×100

Yield (%) of butene dimer=total butene conversion× selectivity of butene dimer/100

The content of phosphorus atoms was measured by one of the analytical methods of total phosphoric acid defined in JIS (Japanese Industrial Standard) K0102 "Testing methods for industrial wastewater", i.e., a method in which the phosphorus is reduced by ascorbic acid to develop color of molybdenum blue and measurement is performed by an absorptiometer. The contents of polar substances in the dimerization reaction product, i.e., isopropanol (IPA), t-butanol (TBA) and acetone (ACE), were measured by a gas chromatograph equipped with FID (measurement device: GC6890 made by Agilent).

Next, an alkaline aqueous solution composed of 2 mg of sodium hydroxide and 50 ml of water was added to 50 ml of the above dimerization reaction product with stirring and the mixture was mixed with stirring at 80° C. for 30 minutes. The alkaline aqueous solution had a pH of 10.9. Subsequently, after allowing to stand for 5 minutes, the alkaline aqueous layer was separated and removed by separation (step 2). Results of measurement of phosphorus atom contents in the dimerization reaction products after the alkaline washing step are shown in Table 2. In all cases, phosphorus atoms have been removed to less than the measurement limit (0.1 ppm by mass).

Next, 50 ml of water was added to the dimerization reaction product prepared in step 2 and the mixture was mixed with stirring at 40° C. for 30 minutes. After allowing to stand, the water layer was separated and removed by separation (step 3). Contents of polar substances in the dimerization reaction product after the water washing, i.e., isopropanol (IPA), t-butanol (TEA) and acetone (ACE) are shown in Table 2. Table 2 shows that the polar substances have been successfully removed.

Examples 2 to 4 and Comparative Example 1

Polar substances were removed using the same dimerization reaction product after alkaline washing as that prepared in step 2 of Example 1 under different conditions in the water washing step (step 3). Results are also shown in Table 2. Table 2 shows that the polar substances such as acetone and alcohol have been successfully removed in Examples 2 to 4 in which the water washing conditions are included within the range of the present invention. It has been shown that polar substances were hardly removed but remained in the dimerization reaction product in Comparative Example 1 in which the water washing temperature was out of the range of the present invention. Although the amount of remaining polar substances are slightly large in Example 4 due to the slightly high washing temperature, the total removal rate has reached not less than 50%, which is much higher than that in Comparative Example 1.

Example 5

The dimerization reaction of olefin (step 1) was carried out in the same manner as in Example 1 except that the temperature at the inlet of the catalyst bed was 60° C. Results are shown in Table 3. The water content in the mixed raw material supplied to the reactor, 300 ppm by mass, is less than the saturated water content at 60° C. of about 1000 ppm by mass.

Subsequently, the dimerization reaction product was subjected to alkaline washing under the same conditions as in step 2 of Example 1 (step 2) and then to water washing under the same conditions as in step 3 of Example 1 (step 3). Results are also shown in Table 3. Since the dimerization reaction product prepared in step 1 had a high phosphorus atom content, the phosphorus atom content in the dimerization reaction product after the completion of step 2 was slightly high at 0.2 ppm by mass. However, phosphoric acid was also removed in step 3, achieving a satisfactory phosphorus atom content in the dimerization reaction product after the completion of step 3 of less than 0.1 ppm by mass. Also, polar substances such as alcohol and acetone have been successfully removed.

Example 6

Step 1 to step 3 were performed under the same conditions as in Example 5 except that the pH of the alkaline aqueous solution was 8.2. Results are shown in Table 3. The removal rate of phosphoric acid was good and polar substances such as alcohol and acetone were satisfactorily removed.

Comparative Example 2

Step 1 through step 3 were performed under the same conditions as in Example 5 except that the alkaline washing temperature in step 2 was 40° C. Results are shown in Table 3. Table 3 shows that since the alkaline washing temperature in step 2 was out of the range of the present invention, the phosphorus atom content in the dimerization reaction product after alkaline washing is high and the remaining phosphorus atoms could not be completely removed in the subsequent water washing step (step 3).

Comparative Example 3

The dimerization reaction of olefin was carried out under the same conditions and by the same procedures as in Example 1 except that the temperature at the inlet of the catalyst bed was 50° C. Results are also shown in Table 3. The water content in the mixed raw material supplied to the reactor, 300 ppm by mass, is less than the saturated water content at 50° C. of about 730 ppm by mass. Table 3 shows that because the conversion of olefin is low, the yield of butene dimer is also low in Comparative Example 3 in which the dimerization reaction temperature was out of the range of the present invention. Moreover, because the reaction temperature was low, more phosphoric acid was eluted, making it impossible to remove the large amount of phosphoric acid in the alkaline washing step. Further, a large amount of polar substances such as alcohol and acetone were mixed into the dimerization reaction product and so removing those substances in the water washing step was considered difficult. In Comparative Example 3, since a large amount of phosphoric acid was eluted into the dimerization reaction product, the phosphoric acid could not be completely removed in the alkaline washing step. For that reason, no water washing step was carried out.

Example 7

Step 1 to step 3 were performed under the same conditions and by the same procedures as in Example 1 except for using the solid phosphoric acid catalyst B. Results are shown in Table 4. The amount of phosphoric acid eluted into the dimerization reaction product was small and phosphoric acid was successfully removed in step 2 and polar substances were successfully removed in step 3.

Example 8

Step 1 to step 3 were performed under the same conditions and by the same procedures as in Example 1 except for using the solid phosphoric acid catalyst C. Results are shown in Table 4. The amount of phosphoric acid eluted into the dimerization reaction product was small and phosphoric acid was successfully removed in step 2 and polar substances were successfully removed in step 3.

Example 9

Step 1 to step 3 were performed under the same conditions and by the same procedures as in Example 1 except that the dimerization reaction temperature was 70° C. Results are shown in Table 4. The amount of phosphoric acid eluted into the dimerization reaction product was small and phosphoric acid was successfully removed in step 2 and polar substances were successfully removed in step 3.

TABLE 2

| | | Example 1 | Example 2 | Example 3 | Example 4 | Comparative Example 1 |
|---|---|---|---|---|---|---|
| outlet of step 1 | water content in hydrocarbon (wt ppm) | 300 | 300 | 300 | 300 | 300 |
| | catalyst | A | A | A | A | A |
| | temperature at inlet of reactor in step 1 (° C.) | 90 | 90 | 90 | 90 | 90 |
| | total olefin conversion (%) | 96 | 96 | 96 | 96 | 96 |
| | selectivity of butene dimer (%) | 75 | 75 | 75 | 75 | 75 |
| | yield of butene dimer (%) | 74 | 74 | 74 | 74 | 74 |
| | content of phosphorus atoms (ppm) | 0.2 | 0.2 | 0.2 | 0.2 | 0.2 |
| | content of TBA (ppm) | 398 | 398 | 398 | 398 | 398 |
| | content of IPA (ppm) | 117 | 117 | 117 | 117 | 117 |
| | content of ACE (ppm) | 50 | 50 | 50 | 50 | 50 |

TABLE 2-continued

|  |  | Example 1 | Example 2 | Example 3 | Example 4 | Comparative Example 1 |
|---|---|---|---|---|---|---|
| outlet of step 2 | temperature of step 2 (° C.) | 80 | 80 | 80 | 80 | 80 |
|  | pH | 10.9 | 10.9 | 10.9 | 10.9 | 10.9 |
|  | content of phosphorus atoms (ppm) | <0.1 | <0.1 | <0.1 | <0.1 | <0.1 |
| outlet of step 3 | temperature of step 3 (° C.) | 40 | 30 | 50 | 100 | 120 |
|  | content of TBA (ppm) | 26 | 17 | 40 | 171 | 350 |
|  | content of IPA (ppm) | 2 | 1 | 2 | 41 | 109 |
|  | content of ACE (ppm) | 3 | 2 | 4 | 23 | 45 |
|  | content of phosphorus atoms | — | — | — | — | — | note:
—: not measured

TABLE 3

|  | No. | Example 5 | Example 6 | Comparative Example 2 | Comparative Example 3 |
|---|---|---|---|---|---|
| outlet of step 1 | water content in hydrocarbon (wtppm) | 300 | 300 | 300 | 300 |
|  | catalyst | A | A | A | A |
|  | temperature at inlet of reactor in step 1 (° C.) | 60 | 60 | 60 | 50 |
|  | total olefin conversion (%) | 81 | 81 | 81 | 61 |
|  | selectivity of butene dimer (%) | 88 | 88 | 88 | 90 |
|  | yield of butene dimer (%) | 71 | 71 | 71 | 55 |
|  | content of phosphorus atoms (ppm) | 5 | 5 | 5 | 100 |
|  | content of TBA (ppm) | 2070 | 2070 | 2070 | 4050 |
|  | content of IPA (ppm) | 596 | 596 | 596 | 1118 |
|  | content of ACE (ppm) | 247 | 247 | 247 | 505 |
| outlet of step 2 | temperature of step 2 (° C.) | 80 | 80 | 40 | 80 |
|  | pH | 10.9 | 8.2 | 10.9 | 10.9 |
|  | content of phosphorus atoms (ppm) | 0.2 | 0.2 | 1 | 3 |
| outlet of step 3 | temperature of step 3 (° C.) | 40 | 40 | 40 |  |
|  | content of TBA (ppm) | 130 | 130 | 130 |  |
|  | content of IPA (ppm) | 9 | 9 | 9 |  |
|  | content of ACE (ppm) | 14 | 14 | 14 |  |
|  | content of phosphorus atoms | <0.1 | <0.1 | 0.5 |  |

TABLE 4

|  | No. | Example 7 | Example 8 | Example 9 |
|---|---|---|---|---|
| outlet of step 1 | water content in hydrocarbon (wtppm) | 300 | 300 | 300 |
|  | catalyst | B | C | A |
|  | temperature at inlet of reactor in step 1 (° C.) | 90 | 90 | 70 |
|  | total olefin conversion (%) | 79 | 82 | 92 |
|  | selectivity of butene dimer (%) | 76 | 72 | 83 |
|  | yield of butene dimer (%) | 60 | 59 | 76 |
|  | content of phosphorus atoms (ppm) | 0.2 | 0.1 | 0.1 |
|  | content of TBA (ppm) | 582 | 273 | 804 |
|  | content of IPA (ppm) | 160 | 79 | 257 |
|  | content of ACE (ppm) | 69 | 31 | 99 |
| outlet of step 2 | temperature of step 2 (° C.) | 80 | 80 | 80 |
|  | pH | 10.9 | 10.9 | 10.9 |
|  | content of phosphorus atoms (ppm) | <0.1 | <0.1 | <0.1 |
| outlet of step 3 | temperature of step 3 (° C.) | 40 | 40 | 40 |
|  | content of TBA (ppm) | 20 | 9 | 52 |
|  | content of IPA (ppm) | 1 | 1 | 4 |
|  | content of ACE (ppm) | 2 | 1 | 6 |
|  | content of phosphorus atoms | — | — | — | note:
—: not measured

INDUSTRIAL APPLICABILITY

According to the present invention, in a dimerization reaction of an olefin using a solid phosphoric acid catalyst, it possible to produce an olefin dimer in which mixed phosphoric acid and polar substances have been efficiently removed by adjusting the water content and the reaction temperature in the reactor, washing the resulting dimerization reaction product with alkali and then with water under a specific condition. Also the present invention can prevent the corrosion of apparatus by phosphoric acid eluted, making it possible to produce an olefin dimer efficiently.

The invention claimed is:

1. A process for producing an olefin dimer comprising:

carrying out a dimerization reaction of an olefin in the presence of a solid phosphoric acid catalyst in which phosphoric acid is supported on inorganic support particles at a reaction temperature of 55 to 300° C. by introducing into a reactor an olefin-containing raw material containing water in an amount of 10 ppm by mass or more and less than the saturated water content at the reaction temperature, thereby preparing a reaction product containing an olefin dimer, washing the reaction product at a temperature of 80° C. or higher using an alkaline substance-containing water adjusted to pH 8 to 13, and washing the reaction product after the alkaline washing with water at a temperature of 0 to 110° C. to remove oxygen-containing compounds selected from an alcohol, a ketone, an ether, and an ester having 3 to 7 carbon atoms, thereby preparing an olefin dimer.

2. The process according to claim 1, wherein the solid phosphoric acid catalyst has a ratio of orthophosphoric acid to the phosphoric acid of 60% by mole or more in terms of phosphorus atoms.

3. The process according to claim 1, wherein the inorganic support particles have an average particle size of 3.0 mm or less.

4. The process according to claim 1, wherein the olefin-containing raw material has a water content of 100 ppm by mass or more and less than the saturated water content at a reaction temperature.

5. The process according to claim 1, wherein the dimerization reaction is carried out in liquid phase.

6. The process according to claim 1, wherein the reaction product is washed with water at a temperature of 0 to 50° C. to remove the oxygen-containing compounds selected from an alcohol, a ketone, an ether, and an ester having 3 to 7 carbon atoms.

7. The process according to claim 1, wherein the olefin is a monoolefin having 3 to 7 carbon atoms.

* * * * *